(12) United States Patent
Souza et al.

(10) Patent No.: US 11,890,124 B2
(45) Date of Patent: Feb. 6, 2024

(54) SYSTEMS AND METHODS FOR LOW-DOSE AI-BASED IMAGING

(71) Applicant: Medtronic Navigation, Inc., Louisville, CO (US)

(72) Inventors: Andre D. A. Souza, Boylston, MA (US); Michael Philip Marrama, Ayer, MA (US); Patrick A. Helm, Milton, MA (US); Mehdi Rahman, North Billerica, MA (US); Kyo C. Jin, Durham, NH (US); Michael D. Ketcha, Baltimore, MD (US)

(73) Assignee: Medtronic Navigation, Inc., Louisville, CO (US)

( * ) Notice: Subject to any disclaimer, the term of this patent is extended or adjusted under 35 U.S.C. 154(b) by 344 days.

(21) Appl. No.: 17/163,719

(22) Filed: Feb. 1, 2021

(65) Prior Publication Data

US 2022/0240879 A1    Aug. 4, 2022

(51) Int. Cl.
*A61B 6/00* (2006.01)
*G06T 11/00* (2006.01)
*G16H 50/20* (2018.01)
*G06N 3/08* (2023.01)

(52) U.S. Cl.
CPC .......... *A61B 6/5205* (2013.01); *A61B 6/5258* (2013.01); *G06N 3/08* (2013.01); *G06T 11/005* (2013.01); *G06T 11/006* (2013.01); *G06T 11/008* (2013.01); *G16H 50/20* (2018.01); *A61B 6/4458* (2013.01); *A61B 6/547* (2013.01);

(Continued)

(58) Field of Classification Search
CPC ... A61B 6/5205; A61B 6/5258; A61B 6/4458; A61B 6/547; A61B 6/563; G16H 50/20; G06N 3/08; G06T 11/005; G06T 11/006; G06T 11/008; G06T 2210/41; G06T 2211/421
See application file for complete search history.

(56) References Cited

U.S. PATENT DOCUMENTS 10,395,397 B2   8/2019  Zhang et al.
10,475,214 B2  11/2019  Fu et al.
(Continued)

FOREIGN PATENT DOCUMENTS

CN   109816742    5/2019
CN   110349234   10/2019
(Continued)

OTHER PUBLICATIONS

Chen et al. "Low-Dose CT via Deep Neural Network," Biomedical Optics Express, Feb. 2017, vol. 8, No. 2, pp. 679-694.
(Continued)

*Primary Examiner* — Vu Le
*Assistant Examiner* — Winta Gebreslassie
(74) *Attorney, Agent, or Firm* — Sheridan Ross P.C.

(57) ABSTRACT

A low-dose imaging method includes receiving a sparse image set of a portion of a patient's anatomy; up-sampling the sparse image set, in the sinogram domain and using a first neural network, to yield an up-sampled sinogram; generating, from the up-sampled sinogram, an initial reconstruction; and removing, from the initial reconstruction and using a second neural network, one or more artifacts in the initial reconstruction to yield a final output volume.

20 Claims, 5 Drawing Sheets

(52) U.S. Cl.
CPC .......... *A61B 6/563* (2013.01); *G06T 2210/41* (2013.01); *G06T 2211/421* (2013.01)

(56) References Cited

U.S. PATENT DOCUMENTS

| | | | | |
|---|---|---|---|---|
| 2004/0009459 | A1* | 1/2004 | Anderson | G06T 19/00 703/11 |
| 2009/0097612 | A1* | 4/2009 | Rauch | A61B 6/4458 378/19 |
| 2014/0010431 | A1* | 1/2014 | Stayman | G06T 11/006 382/131 |
| 2019/0108904 | A1 | 4/2019 | Zhou et al. | |
| 2019/0325621 | A1 | 10/2019 | Wang et al. | |
| 2019/0328348 | A1 | 10/2019 | De Man et al. | |
| 2019/0333219 | A1 | 10/2019 | Xu et al. | |
| 2019/0371018 | A1* | 12/2019 | Ye | G06N 3/08 |
| 2020/0027252 | A1 | 1/2020 | Ye et al. | |
| 2020/0043204 | A1 | 2/2020 | Fu et al. | |
| 2020/0118306 | A1 | 4/2020 | Ye et al. | |
| 2020/0151921 | A1 | 5/2020 | Schildkraut | |
| 2020/0151922 | A1 | 5/2020 | Xu et al. | |
| 2020/0297424 | A1 | 9/2020 | Helm et al. | |
| 2020/0305806 | A1* | 10/2020 | Tang | G06N 3/084 |
| 2020/0311914 | A1* | 10/2020 | Zaharchuk | A61B 6/4417 |
| 2022/0130079 | A1* | 4/2022 | Hu | A61B 6/5282 |
| 2022/0319071 | A1* | 10/2022 | Grass | G06V 10/82 |

FOREIGN PATENT DOCUMENTS

| | | |
|---|---|---|
| CN | 110599420 | 12/2019 |
| CN | 110610198 | 12/2019 |
| CN | 110660123 | 1/2020 |
| CN | 108961237 | 8/2020 |
| EP | 3671646 | 6/2020 |
| EP | 3719750 | 10/2020 |
| KR | 10-2061967 | 1/2020 |
| WO | WO 2019/145149 | 8/2019 |
| WO | WO 2019/183584 | 9/2019 |
| WO | WO 2019/207144 | 10/2019 |

OTHER PUBLICATIONS

Gjesteby et al. "Reducing Metal Streak Artifacts in CT Images via Deep Learning: Pilot Results," The 14th International Meeting on Fully Three-Dimensional Image Reconstruction in Radiology and Nuclear Medicine, Jun. 2017, pp. 611-614.

Lee et al. "A Metal Artifact Reduction Method Using a Fully Convolutional Network in the Sinogram and Image Domains for Dental Computed Tomography," Journal of Digital Imaging, 2020, vol. 33, pp. 538-546.

Lee et al. "A Hybrid Metal Artifact Reduction Method using a Convolutional-neural-network in Computed Tomography," SIIM19 Annual Meeting, Jun. 26-28, 2019, 2 pages.

Lin et al. "DuDoNet: Dual Domain Network for CT Metal Artifact Reduction," arXiv, Jun. 29, 2019, 14 pages.

Schäfer et al. "Modified Parker weights for super short scan cone beam CT," The 14th International Meeting on Fully Three-Dimensional Image Reconstruction in Radiology and Nuclear Medicine, Jun. 2017, pp. 49-52.

Wang et al. "CT-image Super Resolution Using 3D Convolutional Neural Network," Computers & Geosciences, Dec. 2019, vol. 133, article 104314, 26 pages.

Zhang et al. "Convolutional Neural Network based Metal Artifact Reduction in X-ray Computed Tomography," arXiv, Apr. 2018, 1709.01581v2, 13 pages.

* cited by examiner

SYSTEMS AND METHODS FOR LOW-DOSE AI-BASED IMAGING

FIELD

The present technology generally relates to medical imaging, and relates more particularly to the use of artificial intelligence to facilitate low-dose medical imaging.

BACKGROUND

Imaging may be used by a medical provider for diagnostic and/or therapeutic purposes. Certain types of imaging, including computed tomography imaging, utilize X-ray radiation to image internal anatomical elements of a patient. X-ray radiation can have negative effects on patients as well as medical providers.

SUMMARY

Example aspects of the present disclosure include:

A low-dose imaging method, comprising: receiving a sparse image set of a portion of a patient's anatomy; up-sampling the sparse image set, in the sinogram domain and using a first neural network, to yield an up-sampled sinogram; generating, from the up-sampled sinogram, an initial reconstruction; and removing, from the initial reconstruction and using a second neural network, one or more artifacts in the initial reconstruction to yield a final output volume.

Any of the aspects herein, wherein the sparse image set is generated using a cone-beam computed tomography scanner following a particular orbit, and the first neural network has been trained using training images specific to the particular orbit.

Any of the aspects herein, wherein the particular orbit is non-planar.

Any of the aspects herein, wherein the sparse image set comprises twenty-five percent or fewer projections than a full image set.

Any of the aspects herein, wherein the second neural network is trained using simulated images generated using CAD models of at least one of a surgical implant or a surgical instrument.

Any of the aspects herein, wherein the second neural network is trained to remove artifacts caused by metal, beam hardening, and scattering.

Any of the aspects herein, further comprising: applying at least one filter to the up-sampled sinogram.

Any of the aspects herein, wherein the at least one filter utilizes at least one of short-scan weights and a sharpening kernel.

Any of the aspects herein, wherein the portion of the patient's anatomy comprises one or more vertebrae and a surgical implant.

Any of the aspects herein, wherein the initial reconstruction is generated using filtered back-projection.

A method of training a neural network, comprising: receiving an image of an anatomical portion of a subject; receiving a CAD model of a surgical implant; generating a first simulated image based on the image and the CAD model, the first simulated image depicting the surgical implant and the anatomical portion of the subject; modifying the simulated image to include simulated artifacts from metal, beam hardening, and scatter, to yield a second simulated image corresponding to the first simulated image; and providing the second simulated image to a neural network as an example input and the first simulated image to the neural network as an example output.

Any of the aspects herein, wherein the image is an image of an anatomical portion of a cadaver.

Any of the aspects herein, wherein the anatomical portion comprises one or more vertebrae.

Any of the aspects herein, wherein the surgical implant is a screw.

Any of the aspects herein, wherein the image is generated using a cone-based computed tomography scanner.

Any of the aspects herein, further comprising repeating the steps of receiving an image, generating a first simulated image, modifying the simulated image, and providing a plurality of times, each time based on a different image.

Any of the aspects herein, wherein the image comprises a reconstruction of a sinogram.

Any of the aspects herein, wherein the image comprises three adjacent image slices of the anatomical portion of the subject, and the first simulated image is based on a center image slice of the three adjacent image slices.

A system for low-dose imaging, comprising: a cone-based computed tomography imaging device capable of selectively acquiring a normal dose image set and a low dose image set, the low dose image set comprising twenty-five percent or fewer images than the normal dose image set; at least one processor; and a memory storing instructions for execution by the at least one processor. The instructions, when executed, cause the at least one processor to: receive, from the imaging device, a low dose image set of a portion of a patient's anatomy comprising a surgical implant; up-sample the low dose image set, in the sinogram domain and using a first neural network, to yield an up-sampled sinogram; generate, from the up-sampled sinogram and using filtered back projection, an initial reconstruction; and remove, from the initial reconstruction and using a second neural network, one or more artifacts in the initial reconstruction to yield a final output volume.

Any of the aspects herein, wherein the low dose image set is generated using a cone-beam computed tomography scanner following a particular orbit, and the first neural network has been trained using training images specific to the particular orbit.

The details of one or more aspects of the disclosure are set forth in the accompanying drawings and the description below. Other features, objects, and advantages of the techniques described in this disclosure will be apparent from the description and drawings, and from the claims.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as $X_1$-$X_n$, $Y_1$-$Y_m$, and $Z_1$-$Z_o$, the phrase is intended to refer to a single element selected from X, Y, and Z, a combination of elements selected from the same class (e.g., $X_1$ and $X_2$) as well as a combination of elements selected from two or more classes (e.g., $Y_1$ and $Z_o$).

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

Numerous additional features and advantages of the present invention will become apparent to those skilled in the art upon consideration of the embodiment descriptions provided hereinbelow.

BRIEF DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

DETAILED DESCRIPTION

It should be understood that various aspects disclosed herein may be combined in different combinations than the combinations specifically presented in the description and accompanying drawings. It should also be understood that, depending on the example or embodiment, certain acts or events of any of the processes or methods described herein may be performed in a different sequence, and/or may be added, merged, or left out altogether (e.g., all described acts or events may not be necessary to carry out the disclosed techniques according to different embodiments of the present disclosure). In addition, while certain aspects of this disclosure are described as being performed by a single module or unit for purposes of clarity, it should be understood that the techniques of this disclosure may be performed by a combination of units or modules associated with, for example, a computing device and/or a medical device.

In one or more examples, the described methods, processes, and techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors (e.g., Intel Core i3, i5, i7, or i9 processors; Intel Celeron processors; Intel Xeon processors; Intel Pentium processors; AMD Ryzen processors; AMD Athlon processors; AMD Phenom processors; Apple A10 or 10X Fusion processors; Apple A11, A12, A12X, A12Z, or A13 Bionic processors; or any other general purpose microprocessors), graphics processing units (e.g., Nvidia GeForce RTX 2000-series processors, Nvidia GeForce RTX 3000-series processors, AMD Radeon RX 5000-series processors, AMD Radeon RX 6000-series processors, or any other graphics processing units), application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Before any embodiments of the disclosure are explained in detail, it is to be understood that the disclosure is not limited in its application to the details of construction and the arrangement of components set forth in the following description or illustrated in the drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, the present disclosure may use examples to illustrate one or more aspects thereof. Unless explicitly stated otherwise, the use or listing of one or more examples (which may be denoted by "for example," "by way of example," "e.g.," "such as," or similar language) is not intended to and does not limit the scope of the present disclosure.

Intraoperative three-dimensional (3D or 3-D) imaging has enabled measurable improvements in the delivery of spinal implants at the cost of exposing the patient to extra radiation. Low-dose imaging in the presence of metal implants or instruments can have a significant impact on the image quality when using direct reconstruction methods such as filtered back projection (FBP). FBP reconstruction exhibits severe image quality degradation when reconstructing low-dose acquisitions (e.g., acquisitions with fewer X-ray projections). Unlike low-dose artifacts caused by reducing tube current (mA), streaking artifacts due to sparse projection views show non-local, structured noise artifacts that are difficult to remove by using existing image denoising methods. Because of the globally distributed nature of the streaking artifacts, deep neural network architectures may be effective in denoising an initial reconstruction obtained by FBP. The present disclosure describes a 3D low-dose reconstruction method in the presence of metals based on deep learning for cone beam computed tomography (CBCT) systems that delivers improved image quality as compared to traditional FBP reconstruction.

Advantages of using an artificial intelligence (AI)-based method to enable low-dose imaging include: 1) once trained, an AI-based method can quickly denoise an image (in some cases as quickly as approximately 100 ms per image or 20 s per 200-image volume), 2) an AI-based method incorporates much richer information about the image structure than traditional regularization methods, and 3) use low-dose imaging can reduce the cost of x-ray tube usage by as much as 50% or more compared with current low dose protocols.

The present disclosure describes a method that uses, for example, two serially staged deep convolutional neural networks (CNNs) trained using cadavers and clinical datasets with metal implants (e.g., screws, rods, pins) or instruments (e.g., retractors, dilators, cannulas, drills, taps). The input training data for the first-stage (sinogram domain) neural network consists of sparsely-sampled sinograms with an 87.5% reduction in dose. Normal dose sinograms are used as training labels. The second-stage (slice domain) neural network receives slabs of 3 adjacent reconstructed slices with normal dose sinograms and CNN-interpolated sinograms output from the first-stage neural network as input training data and outputs a metal artifact-reduced version of the center slice of the slab. Metal artifact reduced versions of 3D reconstructions with normal dose and augmented images with simulated implants or instruments may be used as training labels.

Methods according to the present disclosure may comprise generating, with a sinogram domain convolutional neural network, an up-sampled sparse acquired sinogram with a trained convolutional neural network; pre-filtering the up-sampled sparse acquired sinogram by logging the sinogram, applying Parker or other short-scan weights, and applying a high-resolution filter kernel; generating a filtered back projection reconstruction using the sinogram; and denoising the filtered back projection reconstruction using a slice domain convolutional neural network. The denoising may comprise denoising in three dimensions.

Use of sharper kernel filters for pre-filtering may beneficially increase spatial resolution as well as the texture of training data. Simulated metal artifact images may be used for training the slice domain convolutional neural network. Cone beam computed tomography phantoms may be used to fine-tune neural network hyperparameters.

The present disclosure also describes methods of training a sinogram-domain and/or slice-domain neural network. In some embodiments, an FBP reconstruction of a pre-filtered, up-sampled sinogram may be provided to a slice domain neural network. The output may then be compared to a "ground truth" image depicting a desired image output, and the loss or difference between the output and the ground truth image may be used to update the neural network. Iterating this process may result in an increasingly accurate slice domain neural network. For purposes of training the slice domain neural network, cadaver images of the lumbar and thoracic spine with and without surgical implants or surgical instruments may be used, as well as cadaver images of the lumbar and thoracic spine augmented with simulated surgical implants. Cadaver images augmented with simulated surgical implants or surgical instruments (e.g., based on a computer-aided design (CAD) model of a surgical implant or surgical instrument, respectively) may be further augmented to include simulated artifacts due to metal (e.g., of the implant or instrument), sparse sampling, beam hardening, and scattering. Such artifacts may already exist, for example, in images of a surgical implant already implanted in a cadaver, or of a surgical instrument being used with a cadaver.

Deep learning can improve the image quality of low-dose imaging in the presence of metal implants or instruments while preserving critical anatomical structures. The use of learning algorithms provides an opportunity to lower patient dose without impacting the clinical utility of images, and to deliver clinical equivalent images with very fast compute times (which may be as low as 80 milliseconds or lower per slice).

Embodiments of the present disclosure beneficially enable the generation of high-quality images using low-dose imaging, which in turn beneficially reduces the radiation exposure of patients and medical providers. Embodiments of the present disclosure also beneficially utilize CAD models of surgical implants and/or instruments to generate simulated training images, which in turn reduces the cost and increases the speed of training a neural network, and yields a neural network capable of removing artifacts from images generated using X-ray technologies.

Embodiments of the present disclosure provide technical solutions to one or more of the problems of (1) reducing the radiation exposure of patients and medical providers without sacrificing clinical utility; (2) accurately training a neural network to remove artifacts (including sparse sampling artifacts, artifacts from metal, beam hardening, and scattering); (3) generating sufficient training data for a neural network without exposing patients to additional radiation; (4) reducing the amount of time required to train a neural network; (5) delivering clinically equivalent images with fast compute times; and (6) reducing the cost of X-ray tube usage without sacrificing clinical utility.

Figure 1:
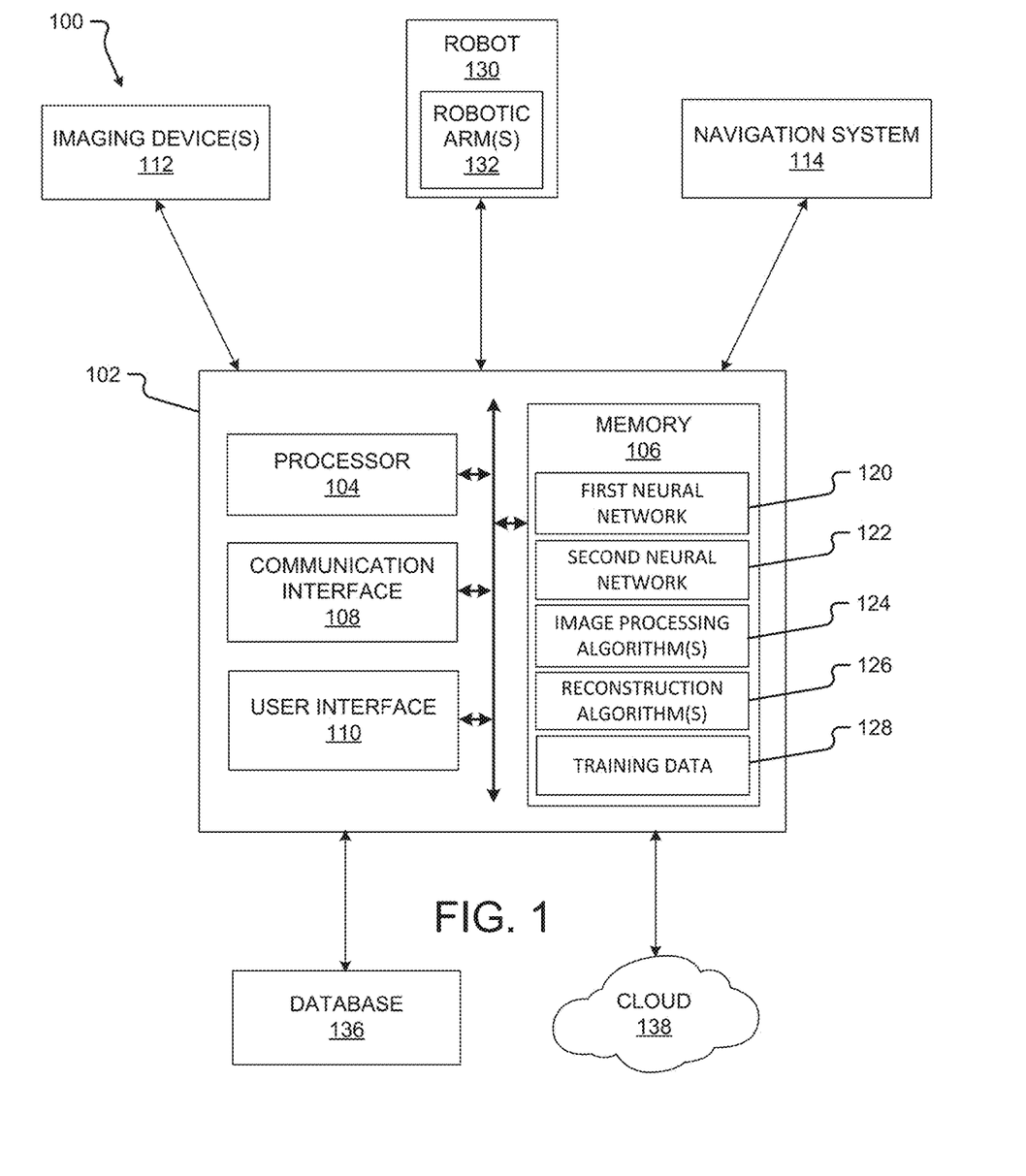
FIG. 1 is a block diagram of a system according to at least one embodiment of the present disclosure.

Turning first to FIG. 1, a block diagram of a system 100 according to at least one embodiment of the present disclosure is shown. The system 100 may be used, for example, to process one or more low-dose image sets of a patient so as to yield an image or image set of comparable or better quality to a full-dose image or image set; to train one or more neural networks; to generate one or more sets of simulated training data; and/or to accomplish or carry out any step of any method disclosed herein. The system 100 of FIG. 1 comprises a computing device 102, one or more imaging devices 112, a navigation system 114, a robot 130, a database 136, and a cloud 138. Systems according to other embodiments of the present disclosure may comprise more or fewer components than the system 100. For example, the system 100 may not include the imaging device 112, the navigation system 114, the robot 130, one or more components of the computing device 102, the database 136, and/or the cloud 138.

The computing device 102 comprises a processor 104, a memory 106, a communication interface 108, and a user interface 110. Computing devices according to other embodiments of the present disclosure may comprise more or fewer components than the computing device 102, including more of any of the foregoing components.

The processor 104 of the computing device 102 may be any processor described herein or any similar processor. The processor 104 may be configured to execute instructions stored in the memory 106, which instructions may cause the processor 104 to carry out one or more computing steps utilizing or based on data received from the imaging device 112, the robot 130, the navigation system 114, the database 136, and/or the cloud 138.

The memory 106 may be or comprise RAM, DRAM, SDRAM, other solid-state memory, any memory described herein, or any other tangible, non-transitory memory for storing computer-readable data and/or instructions. The memory 106 may store information or data useful for completing, for example, any step of the methods 500 and/or 000 described herein, or of any other methods. The memory 106 may store, for example, a first neural network 120, a second neural network 122, one or more image processing algorithms 124, one or more reconstruction algorithms 126, and/or training data 128. Such instructions, algorithms, and/or data may, in some embodiments, be organized into one or more applications, modules, packages, layers, or engines. The algorithms, instructions, and/or data may cause the processor 104 to manipulate and/or analyze data stored in the memory 106 and/or received from or via the imaging device 112, the robot 130, the database 136, the cloud 138, and/or any other source.

The computing device 102 may also comprise a communication interface 108. The communication interface 108 may be used for receiving image data or other information from an external source (such as the imaging device 112, the navigation system 114, the robot 130, the database 136, the cloud 138, and/or any other system or component not part of the system 100), and/or for transmitting instructions, images, or other information to an external system or device (e.g., another computing device 102, the navigation system 114, the imaging device 112, the robot 130, the database 136, the cloud 138, and/or any other system or component not part of the system 100). The communication interface 108 may comprise one or more wired interfaces (e.g., a USB port, an ethernet port, a Firewire port) and/or one or more wireless transceivers or interfaces (configured, for example, to transmit and/or receive information via one or more wireless communication protocols such as 802.11a/b/g/n, Bluetooth, NFC, ZigBee, and so forth). In some embodiments, the communication interface 108 may be useful for enabling the device 102 to communicate with one or more other processors 104 or computing devices 102, whether to reduce the time needed to accomplish a computing-intensive task or for any other reason.

The computing device 102 may also comprise one or more user interfaces 110. The user interface 110 may be or comprise a keyboard, mouse, trackball, monitor, television, screen, touchscreen, and/or any other device for receiving information from a user and/or for providing information to a user. The user interface 110 may be used, for example, to receive a user selection or other user input regarding any step of any method described herein. Notwithstanding the foregoing, any required input for any step of any method described herein may be generated automatically by the system 100 (e.g., by the processor 104 or another component of the system 100) or received by the system 100 from a source external to the system 100. In some embodiments, the user interface 110 may be useful to allow a surgeon or other user to modify instructions to be executed by the processor 104 according to one or more embodiments of the present disclosure, and/or to modify or adjust a setting of other information displayed on the user interface 110 or corresponding thereto.

Although the user interface 110 is shown as part of the computing device 102, in some embodiments, the computing device 102 may utilize a user interface 110 that is housed separately from one or more remaining components of the computing device 102. In some embodiments, the user interface 110 may be located proximate one or more other components of the computing device 102, while in other embodiments, the user interface 110 may be located remotely from one or more other components of the computing device 102.

The imaging device 112 may be operable to image anatomical feature(s) (e.g., a bone, veins, tissue, etc.) and/or other aspects of patient anatomy to yield image data (e.g., image data depicting or corresponding to a bone, veins, tissue, etc.). The image data may be or comprise a preoperative image, a post-operative image, or an image taken independently of any surgical procedure. The imaging device 112 may be capable of taking a 2D image or a 3D image to yield the image data. "Image data" as used herein refers to the data generated or captured by an imaging device 112, including in a machine-readable form, a graphical/visual form, and in any other form. In various examples, the image data may comprise data corresponding to an anatomical feature of a patient, or to a portion thereof. The imaging device 112 may be or comprise, for example, an ultrasound scanner (which may comprise, for example, a physically separate transducer and receiver, or a single ultrasound transceiver), a radar system (which may comprise, for example, a transmitter, a receiver, a processor, and one or more antennae), an O-arm, a C-arm, a G-arm, or any other device utilizing X-ray-based imaging (e.g., a fluoroscope, a CT scanner, or other X-ray machine), a magnetic resonance imaging (MM) scanner, an optical coherence tomography scanner, an endoscope, a telescope, a thermographic camera (e.g., an infrared camera), or any other imaging device 112 suitable for obtaining images of an anatomical feature of a patient. In some embodiments, the imaging device 112 may be a cone beam computed tomography (CBCT) scanner.

X-ray based imaging devices may be configured to selectively operate in a normal-dose mode and a low-dose mode. The normal-dose mode may be the default setting of the imaging device, and may expose a patient to a certain amount of radiation. In some embodiments, the amount of radiation to which a patient is exposed when the imaging device is used in a normal-dose mode may correspond to a regulatory or other standard. When the imaging device is used in the normal-dose mode, the imaging device may generate a set number of images as it passes along a given trajectory (e.g., around a C-arm, O-arm, or similar imaging device, or under the control of a robot such as a robot 130), with each image captured by exposing the patient to a particular amount of radiation, and the total exposure constituting the amount of per-image radiation exposure multiplied by the number of images captured. The low-dose mode may expose the patient to a lower amount of radiation than the normal-dose mode. Embodiments of the present disclosure may utilize low-dose imaging that exposes the patient to 75% or less of the amount of radiation to which a patient would be exposed in a normal-dose mode. The reduction in radiation exposure may be achieved, for example, by capturing fewer images as the imaging device passes along a given trajectory. Thus, the low-dose imaging may yield a sparse image set comprising twenty-five percent or fewer images than an image set resulting from operation of the imaging device in the normal-dose mode.

In some embodiments, the imaging device 112 may comprise more than one imaging device 112. For example, a first imaging device may provide first image data and/or a first image, and a second imaging device may provide second image data and/or a second image. In still other embodiments, the same imaging device may be used to provide both the first image data and the second image data, and/or any other image data described herein. The imaging device 112 may be operable to generate a stream of image data. For example, the imaging device 112 may be configured to operate with an open shutter, or with a shutter that continuously alternates between open and shut so as to capture successive images. For purposes of the present disclosure, unless specified otherwise, image data may be considered to be continuous and/or provided as an image data stream if the image data represents two or more frames per second.

The navigation system 114 may provide navigation for a surgeon and/or a surgical robot during an operation. The navigation system 114 may be any now-known or future-developed navigation system, including, for example, the Medtronic StealthStation™ S8 surgical navigation system or any successor thereof. The navigation system 114 may include a camera or other sensor(s) for tracking one or more reference markers, navigated trackers, or other objects within the operating room or other room in which some or all of the system 100 is located. In various embodiments, the navigation system 114 may be used to track a position and orientation (i.e., pose) of the imaging device 112, the robot 130 and/or robotic arm 132, and/or one or more surgical tools (or, more particularly, to track a pose of a navigated tracker attached, directly or indirectly, in fixed relation to one or more of the foregoing). The navigation system 114 may include a display for displaying one or more images from an external source (e.g., the computing device 102, imaging device 112, or other source) or for displaying an image and/or video stream from the camera or other sensor of the navigation system 114. In some embodiments, the system 100 can operate without the use of the navigation system 114. The navigation system 114 may be configured to provide guidance to a surgeon or other user of the system 100 or a component thereof, to the robot 130, or to any other element of the system 100 regarding, for example, a pose of one or more anatomical elements, and/or whether or not an imaging device is positioned along a proper trajectory (and/or how to move the imaging device onto the proper trajectory), or for any other useful purpose.

The robot 130 may be any surgical robot or surgical robotic system. The robot 130 may be or comprise, for example, the Mazor X™ Stealth Edition robotic guidance system. The robot 130 may be configured to position the imaging device 112 at one or more precise position(s) and orientation(s), and/or to return the imaging device 112 to the same position(s) and orientation(s) at a later point in time. The robot 130 may additionally or alternatively be configured to manipulate a surgical tool (whether based on guidance from the navigation system 114 or not) to accomplish or to assist with a surgical task. The robot 130 may comprise one or more robotic arms 132. In some embodiments, the robotic arm 132 may comprise a first robotic arm and a second robotic arm, though the robot 130 may comprise more than two robotic arms. In some embodiments, one or more of the robotic arms 132 may be used to hold and/or maneuver the imaging device 112. In embodiments where the imaging device 112 comprises two or more physically separate components (e.g., a transmitter and receiver), one robotic arm 132 may hold one such component, and another robotic arm 132 may hold another such component. Each robotic arm 132 may be positionable independently of the other robotic arm.

The robot 130, together with the robotic arm 132, may have, for example, at least five degrees of freedom. In some embodiments the robotic arm 132 has at least six degrees of freedom. In yet other embodiments, the robotic arm 132 may have fewer than five degrees of freedom. Further, the robotic arm 132 may be positioned or positionable in any pose, plane, and/or focal point. The term "pose," as used herein, refers to both a position and an orientation. As a result, an imaging device 112, surgical tool, or other object held by the robot 130 (or, more specifically, by the robotic arm 132) may be precisely positionable in one or more needed and specific positions and orientations.

In some embodiments, reference markers (i.e., navigation markers) may be placed on the robot 130 (including, e.g., on the robotic arm 132), the imaging device 112, or any other object in the surgical space. The reference markers may be tracked by the navigation system 114, and the results of the tracking may be used by the robot 130 and/or by an operator of the system 100 or any component thereof. In some embodiments, the navigation system 114 can be used to track other components of the system (e.g., imaging device 112) and the system can operate without the use of the robot 130 (e.g., with the surgeon manually manipulating the imaging device 112 and/or one or more surgical tools, based on information and/or instructions generated by the navigation system 114, for example).

The system 100 or similar systems may be used, for example, to carry out one or more aspects of any of the methods 500 and/or 600 described herein. The system 100 or similar systems may also be used for other purposes. In some embodiments, a system 100 may be used to generate and/or display a 3D model of an anatomical feature or an anatomical volume of a patient. For example, the robotic arm 132 (controlled by a processor of the robot 130, the processor 104 of the computing device 102, or some other processor, with or without any manual input) may be used to position the imaging device 112 at a plurality of predetermined, known poses, so that the imaging device 112 can obtain one or more images at each of the predetermined, known poses. Because the pose from which each image is taken is known, the resulting images may be assembled together to form or reconstruct a 3D model. The system 100 may update the model based on information (e.g., segmental tracking information) received from the imaging device 112, as described elsewhere herein.

Figure 2A:
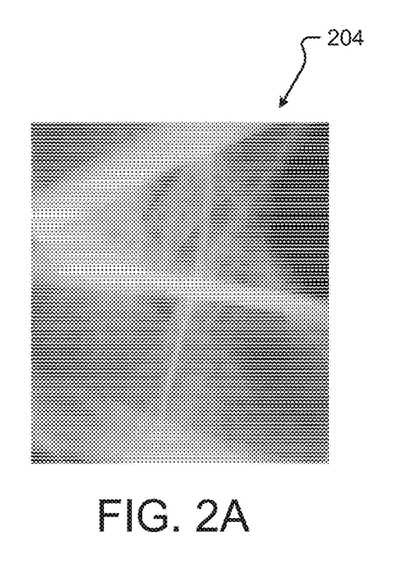
FIG. 2A is a sinogram of a sparse image set.

FIG. 2A is a sinogram 204 of a sparse image set. Embodiments of the present disclosure involve obtaining a sparse image set and generating a sinogram of the sparse image set. The sparse image set may be obtained, for example, from an imaging device such as the imaging device 112. The imaging device may be an O-arm, C-arm, or any other device that utilizes X-ray technology to generate images. More specifically, the imaging device may be a CBCT scanner. The sparse image set is an image set obtained using less than a full dose of radiation. In other words, the sparse image set contains fewer images than a full image set, such that the subject of the images is exposed to radiation fewer times than would be required to obtain a full image set, with the end result being a lower exposure to radiation than if a full image set had been used. The sparse image set may contain, for example, a number of images that is less than a number of images in a full image set by fifty percent or less, or by thirty percent or less, or by twenty-five percent or less, or by twenty percent or less, or by fifteen percent or less, or by twelve and a half percent or less, or by ten percent or less, or by five percent or less. These percentages also correspond to an amount of radiation to which a subject is exposed to obtain the sparse image set, relative to a full dose of radiation. In other words, the amount of radiation to which the subject is exposed may be fifty percent or less, or thirty percent or less, etc. than a full dose of radiation used to obtain a full image set.

Figure 2B:
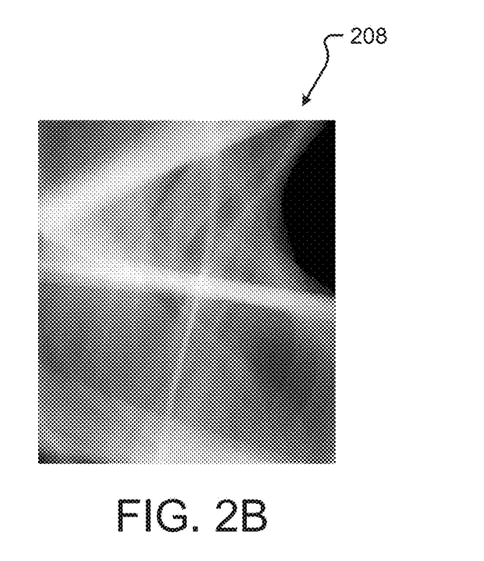
FIG. 2B is an up-sampled sinogram output from a neural network.

As seen in FIG. 2A, a sinogram 204 generated from a sparse image set (referred to herein as a "low-dose sinogram") comprises a plurality of lines where data is missing due to the lower number of images used to generate the sinogram. The low-dose sinogram—which may reflect, for example, an 87.5% reduction in dose as compared to a normal-dose sinogram—has inferior image quality to an up-sampled sinogram 208 such as that shown in FIG. 2B (which has been up-sampled to have substantially the same quality as a normal-dose sinogram). However, when provided with a low-dose sinogram as an input, artificial intelligence may be used to generate an up-sampled sinogram 208 having substantially the same quality as a normal-dose sinogram. More specifically, machine learning may be used to determine how to modify a low-dose sinogram 204 to yield an up-sampled sinogram 208 with improved quality. For example, a neural network (which may be, for example, a convolutional neural network, a recurrent neural network, or a generative adversarial neural network) may be provided a plurality of low-dose sinograms as training data, and a plurality of corresponding normal-dose sinograms as training labels or "ground truth" data. In some embodiments, tens, hundreds, or even thousands of pairs of low-dose sinograms and corresponding normal-dose sinograms may be used to train a neural network. Based on these inputs, the neural network may generate one or more algorithms useful for interpolating or otherwise filling in data missing from a low-dose sinogram, and thus for generating an up-sampled sinogram 208 (having a quality equal or similar to a normal-dose sinogram) based on a low-dose sinogram 204. In some embodiments of the present disclosure, the first neural network 120 of FIG. 1 is a sinogram domain neural network configured to receive low-dose sinograms 204 and to output up-sampled sinograms 208, and trained for such purpose as described above.

Figure 3A:
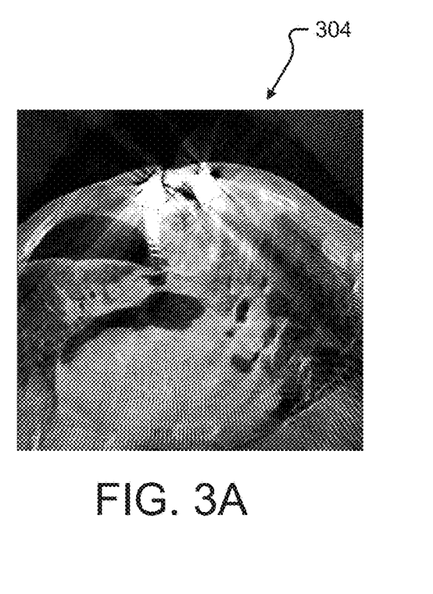
FIG. 3A is an image reconstructed from a sinogram.
Figure 3B:
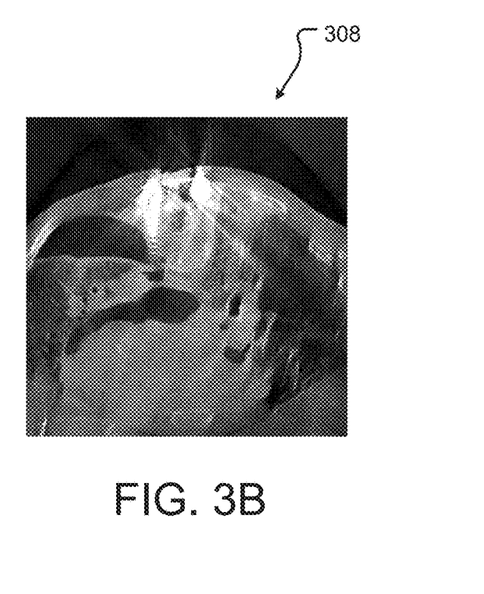
FIG. 3B is a corrected image output from a neural network.

FIG. 3A depicts an image 304 reconstructed from an up-sampled sinogram. The reconstruction may have been carried out using one or more reconstruction algorithms 126—which may be or include, for example, a filtered back projection (FBP) reconstruction algorithm. As evident from FIG. 3A, low-dose imaging in the presence of metal implants and/or instruments can have a significant impact on the image quality when using direct reconstruction methods such as FBP. Unlike low-dose artifacts caused by reducing tube current (mA), streaking artifacts due to sparse projection views show non-local, structured noise artifacts that are difficult to remove by using existing image denoising methods. Because of the globally distributed nature of the streaking artifacts, artificial intelligence, and more particularly machine learning, and even more particularly, neural networks, can be effective in denoising an initial reconstruction obtained by FBP, yielding a corrected image 308 as shown in FIG. 3B.

Figure 4A:
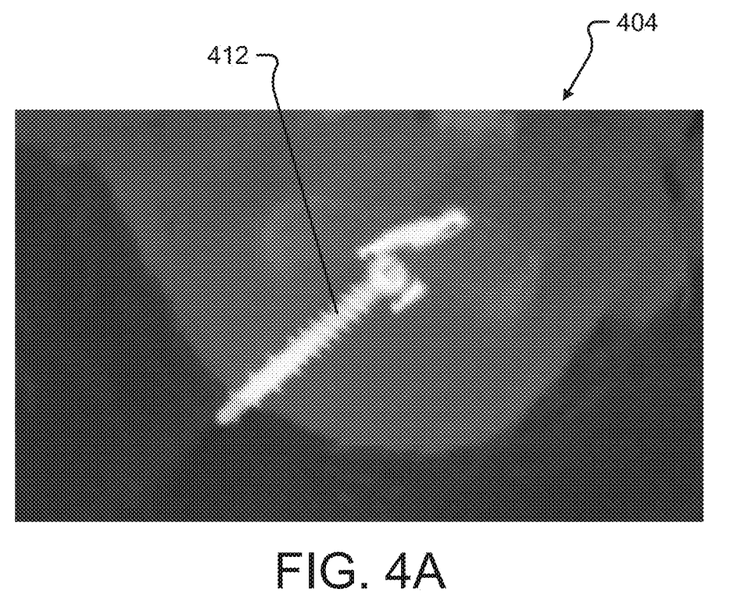
FIG. 4A is a simulated image for training a neural network.
Figure 4B:
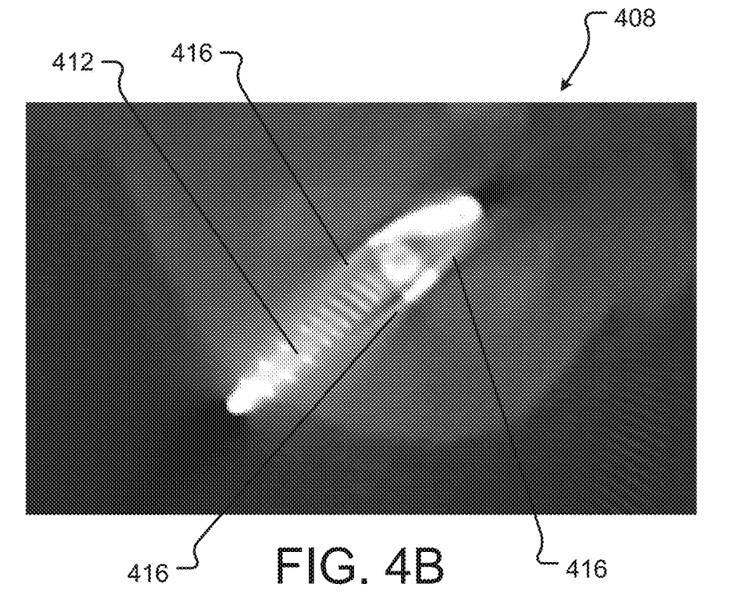
FIG. 4B is a simulated image for training a neural network.

For example, a convolutional network or any other neural network (including any neural network identified herein) may be trained to denoise an FBP reconstruction of an up-sampled sinogram using actual FBP reconstructions of an up-sampled sinogram (such as, for example, the image 304 of FIG. 3A); FBP reconstructions of normal-dose sinograms and/or corrected FBP reconstructions such as the image 308 of FIG. 3B; simulated images (such as the image 404 of FIG. 4A) in which a profile of an implant 412 (based on a CAD model of the implant) is superimposed on an FBP reconstruction; and augmented simulated images (such as the augmented image 408 of FIG. 4B) in which simulated artifacts 416 (e.g., resulting from metal, beam hardening, and scatter) have been added to the simulated image. The FBP reconstruction of the up-sampled sinogram as well as the further-processed versions of the simulated images may be provided to the neural network as example inputs, and the FBP reconstructions of normal-dose sinograms as well as the original simulated images (showing the profile of the implant, without any simulated artifacts) are provided to the neural network as example "ground truth" outputs. Based on these example inputs and outputs, the neural network may generate one or more algorithms for denoising and otherwise removing artifacts from an FBP reconstruction (or any other type of reconstruction represented in the training data) of an up-sampled sinogram.

In some embodiments, example input training data comprising slabs of three adjacent reconstructed slices of FBP reconstructions (of both up-sampled sinograms and normal-dose sinograms) may be provided for training purposes to the neural network, and example output training data comprising 2D slices of the corresponding center slides of the input 3D slabs may be provided for training purposes to the neural network. The 3D spatial context from the surrounding slides may beneficially facilitate the learning by the network of the noise patterns and artifacts in the training data images.

Figure 5:
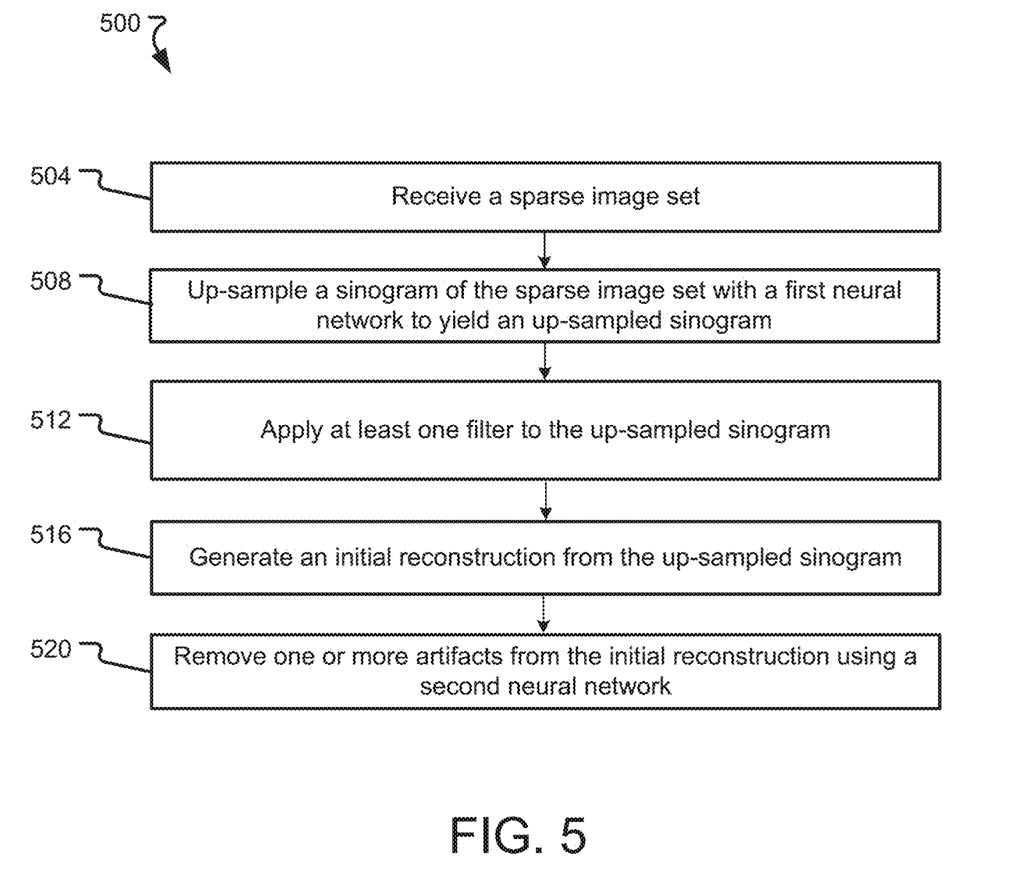
FIG. 5 is a flowchart of a method according to at least one embodiment of the present disclosure.

Turning now to FIG. 5, a low-dose imaging method 500 (and/or one or more steps thereof) may be carried out or otherwise performed, for example, by at least one processor. The at least one processor may be the same as or similar to the processor(s) 104 of the computing device 102 described above. The at least one processor may be part of a robot (such as a robot 130) or part of a navigation system (such as a navigation system 114). A processor other than any processor described herein may also be used to execute the method 500. The at least one processor may perform the method 500 by executing instructions stored in a memory such as the memory 106. The instructions may correspond to one or more steps of the method 500 described below. The instructions may cause the processor to execute one or more algorithms, such as one or more image processing algorithms 124 and/or one or more reconstruction algorithms 126. The method 500 may utilize a first neural network 120, a second neural network 122, and/or training data 128.

The method 500 comprises receiving a sparse image set (step 504). The sparse image set may be generated using an imaging device 112, or any other imaging device. The imaging device may be, for example, an O-arm or a C-arm. In some embodiments, the imaging device may be a CBCT scanner. The sparse image set comprises a plurality of images, each taken at a different angle relative to the subject. However, the sparse image set comprises fewer images than full image set. For example, the sparse image set may comprise fifty percent or less, or thirty percent or less, or twenty-five percent or less, or twenty percent or less, or fifteen percent or less, or twelve and a half percent or less, or ten percent or less, or five percent or less, of the total number of images in a full image set. Thus, if a full image set comprises 200 images, then the sparse image set may comprise, for example, one hundred images or fewer, sixty images or fewer, fifty images or fewer, forty images or fewer, thirty images or fewer, twenty-five images or fewer, twenty images or fewer, or ten images or fewer.

The use of a sparse image set beneficially reduces the radiation exposure of the subject of the images. Each image is generated by exposing the patient to a particular amount of radiation, and so the fewer images obtained, the lower the patient's radiation exposure. For purposes of the present disclosure, a full image set corresponds to a normal or full dose of radiation, which is the standard amount of radiation to which a patient is exposed during a normal spin (or other operation) of the imaging device.

The sparse image set depicts a portion of a patient's anatomy and a metal implant (and/or a metal instrument) positioned therein. For example, the sparse image set may depict a portion of a patient's spine (including, for example, one or more vertebrae), together with one or more screws implanted in the patient's spine, and/or with a retractor being used to hold open an incision. Moreover, the sparse image set may comprise a plurality of images captured as the imaging device moves along a planar orbit around the subject, or along a non-planar orbit. (Such motion may occur, for example, as an imaging probe moves along a track of the imaging device, as with an O-arm or C-arm, or as a robot such as the robot 130 moves the imaging device along a particular orbit or trajectory.) For example, the imaging device may move along a non-planar orbit that resembles the shape of stitching on a professional baseball. More broadly, the imaging device may move not just around a longitudinal axis of a patient (e.g., an axis extending from the patient's head to the patient's feet), but also parallel to that axis as it acquires the sparse image set.

The method 500 also comprises up-sampling a sinogram of the sparse image set with a first neural network to yield an up-sampled sinogram (step 508). The first neural network may be, for example, a first neural network 120. The first neural network may be a convolutional neural network, a reconstructive neural network, a generative adversarial neural network, or any other neural network capable of accomplishing the functions of the first neural network as described herein. The first neural network may have been specifically trained using images acquired along a trajectory or orbit identical to that used for acquisition of the sparse image set received in the step 504.

More specifically, the first neural network may have been trained using training data such as the training data 128 comprising one or more sinograms of sparse image sets (e.g., low-dose sinograms) as example inputs, and a plurality of corresponding normal-dose sinograms as training labels or "ground truth" data. Based on these inputs, the neural network may have generated one or more algorithms useful for interpolating or otherwise filling in data missing from a low-dose sinogram, and thus for generating an up-sampled sinogram (having a quality equal or similar to the normal-dose sinogram of FIG. 2B) based on a low-dose sinogram such as a sinogram of the sparse image set received in the step 504.

The sinogram of the sparse image set may be generated using any known method of generating sinograms. Because the image set is sparse, the sinogram of the sparse-image set will comprise a plurality of lines passing therethrough, representing data missing from the sparse image set (e.g., corresponding to the images that would have been included in a full image set but were not acquired for the sparse image set). The sinogram of the sparse image set is provided to the first neural network, which outputs an up-sampled sinogram. The up-sampled sinogram is a sinogram of higher image quality than the original sinogram. In some embodiments, the up-sampled sinogram may have a quality as high as that of a sinogram of a full image set.

The method 500 also comprises applying at least one filter to the up-sampled sinogram (step 512). The applying at least one filter may comprise, for example, applying Parker or other short-scan weights to the sinogram to account for oversampling and/or undersampling of portions of the patient's anatomy. The short-scan weights may be used, for example, to correct undersampling resulting from utilizing a sparse image set. The applying at least one filter may also comprise applying a high-resolution filter kernel to enhance soft tissue edges represented in the sinogram.

The method 500 also comprises generating an initial reconstruction from the up-sampled sinogram (step 516). The initial reconstruction may be generated, for example, using filtered back projection, although other reconstruction methods may also be used. In some embodiments, the type of reconstruction used in the step 516 corresponds to a type of reconstruction used to generate training data for a second neural network used in connection with the step 520 discussed below. The initial reconstruction may use one or more reconstruction algorithms 126.

The initial reconstruction comprises one or more artifacts resulting from metal, beam hardening, and/or scatter. The initial reconstruction may also comprise noise or other undesirable effects resulting from the use of an up-sampled sinogram, rather than a sinogram resulting from a full image set, for the reconstruction. In some embodiments, the reconstruction method, whether FBP or otherwise, may introduce imperfections into the initial reconstruction. In any event, the initial reconstruction may have a lower clinical value than a reconstruction generated from a sinogram created using a full image set. The reconstruction may be or comprise a three-dimensional image volume, and may further comprise a plurality of two-dimensional images or image "slices."

The method 500 also comprises removing one or more artifacts from the initial reconstruction using a second neural network (step 520). The second neural network, which may be a second neural network 122, is different than the first neural network, and is specifically trained to remove artifacts from (or to otherwise denoise) a reconstructed image. The second neural network may be trained for example, using the method 600 described below. Whereas the first neural network of the step 508 operates in the sinogram domain, the second neural network of the step 520 operates in the slice domain. More specifically, the second neural network receives as an input one or more two-dimensional images or image slices, and outputs at least one two-dimensional image or image slice. In some embodiments, the second neural network receives as an input three adjacent image slices, and outputs a single image slice corresponding to the center slice of the three adjacent image slices. The output image slice is a corrected image slice in which one or more artifacts (whether resulting from the presence of metal in the image, beam hardening, scatter, and/or any other cause) have been reduced or removed, yielding two-dimensional image of comparable clinical value as an image generated using a full image set and conventional image processing techniques.

The present disclosure encompasses embodiments of the method 500 that comprise more or fewer steps than those described above, and/or one or more steps that are different than the steps described above.

Figure 6:
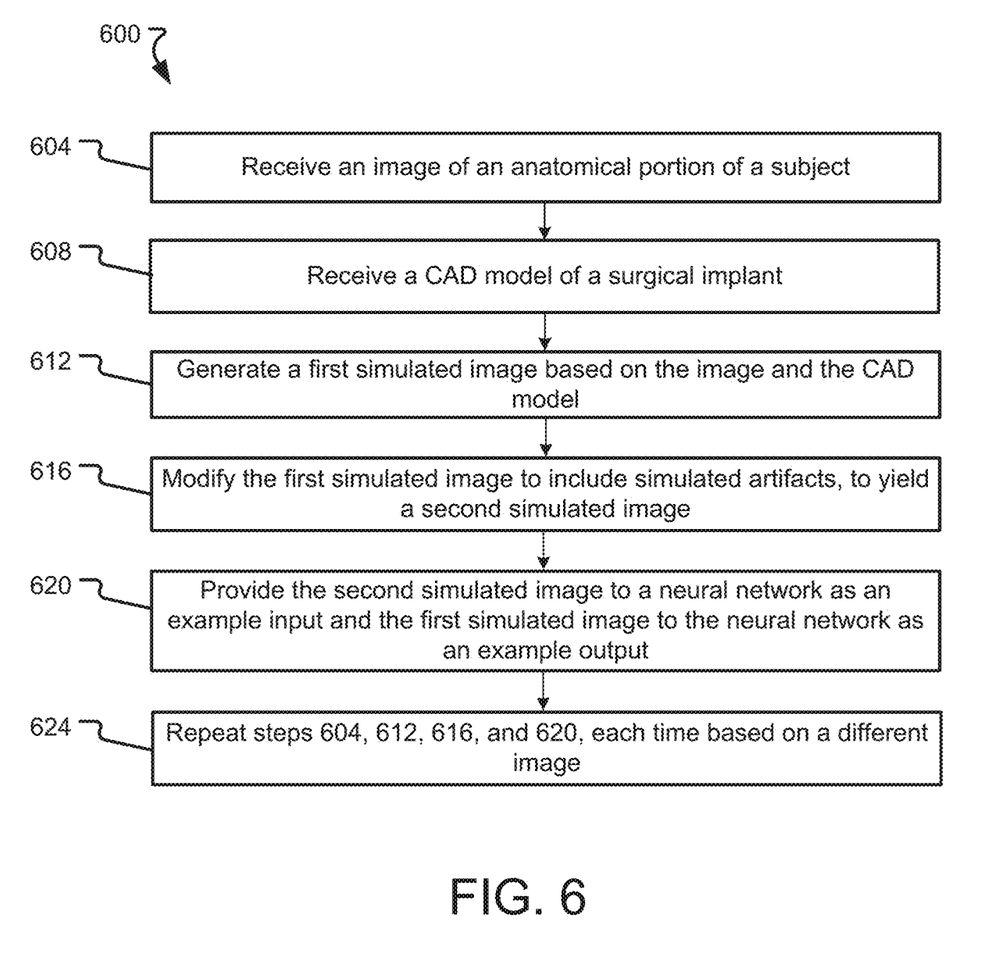
FIG. 6 is a flowchart of another method according to at least one embodiment of the present disclosure.

FIG. 6 depicts a method 600 for training a neural network. The method 600 (and/or one or more steps thereof) may be carried out or otherwise performed, for example, by at least one processor. The at least one processor may be the same as or similar to the processor(s) 104 of the computing device 102 described above. The at least one processor may be part of a robot (such as a robot 130) or part of a navigation system (such as a navigation system 114). A processor other than any processor described herein may also be used to execute the method 600. The at least one processor may perform the method 600 by executing instructions stored in a memory such as the memory 106. The instructions may correspond to one or more steps of the method 600 described below. The instructions may cause the processor to execute one or more algorithms, such as one or more image processing algorithms 124 and/or one or more reconstruction algorithms 126. The method 600 may utilize a first neural network 120, a second neural network 122, and/or training data 128.

The method 600 comprises receiving an image of an anatomical portion of a subject (step 604). The image may be a three-dimensional image or a two-dimensional image. The image may be received from an imaging device such as the imaging device 112, from a memory such as the memory 106, from a database such as the database 136, or from a network such as the cloud 138. The image may be received via, for example, a communication interface such as the communication interface 108. The image may be an image of a portion of an anatomy of a subject. in some embodiments, the subject may be a living person, while in other embodiments, the subject may be a cadaver. The image may depict, for example, one or more vertebrae of a spine of the subject, although the image may additionally or alternatively depict one or more other anatomical elements of the subject. The received image may be, in some embodiments, a set of three adjacent images from a 3D volume.

In some embodiments, the image may be an image generated from a normal-dose sinogram using filtered back projection. In other embodiments, the image may be an image generated from an up-sampled sinogram using filtered back projection. In still other embodiments, the image may be any image generated from a sinogram using filtered back projection. In yet further embodiments, the image may be any image generated from a sinogram using a reconstruction technique or algorithm other than filtered back projection. The initial image set used to generate the sinogram may be obtained using cone beam computed tomography (CBCT) imaging.

The method 600 also comprises receiving a CAD (computer-aided design) model of a surgical implant (step 608). The CAD model may be 3D or 2D, may be generated using any CAD program, and may be provided in any format suitable for achieving the function described herein. The CAD model may be received from an external computing device, from a memory such as the memory 106, from a database such as the database 136, or from a network such as the cloud 138. The CAD model may be received via, for example, a communication interface such as the communication interface 108. The CAD model may be a model of any medical implant, including a pedicle or other type of screw, a rod, a pin, an interbody cage, or any other implant. In some embodiments, the CAD model may be of a surgical instrument or other object rather than a surgical implant. For example, the CAD model may be a model of scissors, retractors, spinal clamps, vertebral body stenting system leads, or other instruments or objects that may be located within an intraoperative image.

The method 600 also comprises generating a first simulated image based on the image and the CAD model (step 612). The first simulated image comprises the image received in the step 604 augmented with the CAD model received in the step 608. Where the image received in the step 604 is a 3D image, a 3D CAD model of the implant or instrument (or a 3D image or representation of the implant or instrument generated using the 3D CAD model) may be positioned in the 3D image in a pose (e.g., a position and orientation) that corresponds to a pose in which the implant or instrument might actually be implanted within or used in connection with a patient. Alternatively, a 2D image slice may be extracted or otherwise obtained from or generated using the 3D image, and a 2D CAD model of the implant or instrument (or a 2D representation of the implant or instrument, generating using a 3D or a 2D CAD model) may be positioned in the image in a pose (e.g., a position and orientation) that corresponds to a pose in which the implant might actually be implanted within, or in which the instrument might actually be used in connection with, a patient.

In some embodiments, such as where the image received in the step 604 is a set of three adjacent images from an image volume, the first simulated image may likewise comprise three simulated images, each augmented based on the CAD model received in the step 608. In still other embodiments, the first simulated image may comprise three adjacent images, but only the center image may be augmented based on the CAD model received in the step 608.

As noted above, in some embodiments a representation of an implant or instrument, generated based on a CAD model of the implant or instrument, is added to the image received in the step 604, rather than the CAD model itself. The representation of the implant or instrument may be, for example, a representation that reflects the way the implant or instrument itself would appear in images of the same type (e.g., the same imaging modality) as the image. Thus, for example, where the image is an X-ray image, the representation may be a bright profile of the implant or instrument (such as the bright implant profile 412 in FIG. 4A). In some embodiments, the representation of the implant or instrument may be an actual image obtained at least in part using an imaging device of the same imaging modality used to obtain the image received in the step 604. In other words, where the image received in the step 604 is an X-ray image, the representation of the implant or instrument that is added to that image may be an X-ray image of an actual implant or instrument, rather than a simulated X-ray image generated using a CAD model of the implant or instrument.

Regardless of how the representation of the implant or instrument is generated, the result of the step 612 is a first simulated image showing the implant or instrument in a particular pose on the image received in the step 604. The step 612 beneficially avoids any need for the implant or instrument to actually be implanted in or used with a subject (whether a cadaver or a living patient) and then imaged to obtain needed training data.

The method 600 also comprises modifying the first simulated image to include simulated artifacts, to yield a second simulated image (step 616). While the first simulated image comprises a "clean" representation of the implant or instrument (e.g., without artifacts), the second simulated image comprises a "noisy" representation of the implant or instrument, in which typical or expected artifacts have been added. The second simulated image thus represents an image that might actually be generated by an imaging device prior to any processing of that image to remove artifacts. The artifacts added to the first simulated image to yield the second simulated image may be or include, for example, metal artifacts, and/or artifacts resulting from sparse sampling, beam hardening, and/or scatter.

Similarly to the step 612, in some embodiments, the addition of artifacts to the first simulated image may be based on an actual image obtained at least in part using an imaging device of the same imaging modality used to obtain the image received in the step 604. In other words, where the image received in the step 604 is an X-ray image, the addition of artifacts to the representation of the implant or instrument may be based on actual artifacts from an X-ray image of an actual implant or instrument in a subject, rather than from simulated artifacts generated using, for example, a CAD model of the implant.

In some embodiments, artificial intelligence may be used to generate the simulated artifacts in the second simulated image. In other embodiments, one or more filters may be applied to the first simulated image (or specifically to the representation of the implant or instrument in the first simulated image), and/or other image processing techniques may be utilized to generate the simulated artifacts.

The method 600 also comprises providing the second simulated image to a neural network as an example input and the first simulated image to the neural network as an example output (step 620). The neural network may be a convolutional neural network, a recurrent neural network, a generative adversarial neural network, or any other type of neural network. In some embodiments, machine learning of a form other than a neural network may be utilized for purposes of the step 620. In still other embodiments, artificial intelligence of a form other than machine learning may be utilized for purposes of the step 620.

The first and second simulated images are provided to the neural network as training data, with the purpose of training the neural network to receive a raw image of an implant or instrument in or proximate a patient (e.g., an image comprising artifacts, such as the second simulated image) and to output a processed image of the implant or instrument in or proximate the patient showing a "clean" representation of the implant or instrument (e.g., an image from which one or more artifacts have been removed, which may be similar in appearance to the first simulated image). By comparing the first and second simulated images, the neural network can identify patterns and develop one or more algorithms for modifying a noisy image (e.g., similar to the second simulated image) by interpolating missing information and removing artifacts to output a clean image (e.g., similar to the first simulated image). In some embodiments, the first and second simulated images may be stored in the memory 106 of a computing device 102 as training data 128.

The method 600 also comprises repeating steps 604, 612, 616, and 620, each time based on a different image (step 624). The repeating enables the neural network to receive additional training data in the form of pairs of simulated images, one noisy and one clean, from which to develop one or more algorithms for removing unwanted artifacts from input images. In some embodiments, each repetition of the identified steps utilizes the same CAD model. As a result, the neural network's training is specific to the implant or instrument corresponding to the CAD model of the step 608. Even so, the neural network may be used in connection with images depicting a different implant or instrument; however, the output image may not be as high quality as an image output from the neural network based on an input image that depicts the implant or instrument used for training the neural network. In still further embodiments, the neural network may be trained using a plurality of different CAD models. However, in such embodiments, a larger set of training data may be required, with the size of the training data based on the number of different CAD models used.

The present disclosure encompasses embodiments of the method 600 that comprise more or fewer steps than those described above, and/or one or more steps that are different than the steps described above.

Although embodiments of the present disclosure have been described in connection with the use of X-ray imaging, one or more aspects of the present disclosure may be useful with magnetic resonance imaging and/or any other type of imaging that induces artifacts and/or where sparse image acquisition (whether to lower the dose of some kind of radiation or to reduce the amount of time required to acquire images) is desirable. With respect to artifacts specifically, the use of CAD models or other prior knowledge of an implant, instrument, or other object expected to be found in an imaging field of view may be used, in accordance with embodiments of the present disclosure, to remove undesirable artifacts.

Additionally, although embodiments of the present disclosure have been described as utilizing neural networks, other embodiments of the present disclosure may utilize machine learning systems other than neural networks, or different artificial intelligence systems altogether. Similarly, although specific neural network architectures have been identified by way of example, any neural network architecture suitable for accomplishing the purposes of the present disclosure as described herein may be used in embodiments of the present disclosure.

Once a neural network or other form of artificial intelligence is trained as disclosed herein, clinically equivalent images may be generated with very fast compute times (e.g., less than 500 ms per image slice, or less than 100 ms per image slice, or less than 80 ms per image slice, or less than 50 ms per image slice) while drastically lowering the patient dose of radiation.

As noted above, the present disclosure encompasses methods with fewer than all of the steps identified in FIGS. 5 and 6 (and the corresponding description of the methods 500 and 600), as well as methods that include additional steps beyond those identified in FIGS. 5 and 6 (and the corresponding description of the methods 500 and 600). The present disclosure also encompasses methods that comprise one or more steps from one method described herein, and one or more steps from another method described herein.

The foregoing is not intended to limit the disclosure to the form or forms disclosed herein. In the foregoing Detailed Description, for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, with each claim standing on its own as a separate preferred embodiment of the disclosure.

Moreover, though the foregoing has included description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A low-dose imaging method, comprising:
   receiving a sparse image set of a portion of a patient's anatomy, wherein the sparse image set comprises a plurality of globally-distributed artifacts;
   up-sampling the sparse image set, in a sinogram domain and using a first neural network trained in the sinogram domain, to yield an up-sampled sinogram in which the first neural network has filled in at least some of the plurality of globally-distributed artifacts;
   generating, from the up-sampled sinogram, an initial reconstruction; and
   removing, from the initial reconstruction and using a second neural network trained in a slice domain, one or more artifacts in the initial reconstruction to yield a final output volume.

2. The low-dose imaging method of claim 1, wherein the sparse image set is generated using a cone-beam computed tomography scanner following a particular orbit, and the first neural network has been trained using training images specific to the particular orbit.

3. The low-dose imaging method of claim 2, wherein the particular orbit is non-planar.

4. The low-dose imaging method of claim 1, wherein the sparse image set comprises twenty-five percent or fewer projections than a full image set.

5. The low-dose imaging method of claim 1, further comprising:
   applying at least one filter to the up-sampled sinogram.

6. The low-dose imaging method of claim 5, wherein the at least one filter utilizes at least one of short-scan weights and a sharpening kernel.

7. The low-dose imaging method of claim 5, wherein the applying at least one filter comprises applying a high-resolution filter kernel to enhance soft tissue edges represented in the up-sampled sinogram.

8. The low-dose imaging method of claim 1, wherein the portion of the patient's anatomy comprises one or more vertebrae and a surgical implant.

9. The low-dose imaging method of claim 1, wherein the initial reconstruction is generated using filtered back-projection.

10. The low-dose imaging method of claim 1, wherein the first neural network comprises at least one of a convolutional neural network, a reconstructive neural network, and a generative adversarial neural network.

11. The low-dose imaging method of claim 1, wherein the one or more artifacts comprise a metal artifact.

12. The low-dose imaging method of claim 1, wherein the initial reconstruction comprises at least three adjacent image slices and wherein the second neural network outputs a correlating single image slice for the at least three adjacent image slices in which the one or more artifacts are removed.

13. The low-dose imaging method of claim 1, wherein at least one of the first neural network and the second neural network comprises a convolutional neural network.

14. A system for low-dose imaging, comprising:
   a cone-based computed tomography imaging device capable of selectively acquiring a normal dose image set and a low dose image set, the low dose image set comprising twenty-five percent or fewer images than the normal dose image set;
   at least one processor; and
   a memory storing data for execution by the at least one processor that, when executed, cause the at least one processor to:
      receive, from the imaging device, a low dose image set of a portion of a patient's anatomy comprising a surgical implant, wherein the low dose image set comprises a plurality of globally-distributed artifacts;
      up-sample the low dose image set, in a sinogram domain and using a first neural network trained in the sinogram domain, to yield an up-sampled sinogram in which the first neural network has filled in at least some of the plurality of globally-distributed artifacts;
      generate, from the up-sampled sinogram and using filtered back projection, an initial reconstruction; and
      remove, from the initial reconstruction and using a second neural network trained in a slice domain, one or more artifacts in the initial reconstruction to yield a final output volume.

15. The system of claim 14, wherein at least one of the first neural network and the second neural network comprises a convolutional neural network.

16. The system of claim 14, wherein the low dose image set is generated using a cone-beam computed tomography scanner following a particular orbit, and the first neural network has been trained using training images specific to the particular orbit.

17. The system of claim 16, wherein the particular orbit is non-planar.

18. The system of claim 14, wherein the initial reconstruction comprises at least three adjacent image slices and wherein the second neural network outputs a correlating single image slice for the at least three adjacent image slices in which the one or more artifacts are removed.

19. The system of claim 14, wherein the initial reconstruction is generated using filtered back projection.

20. The system of claim 14, wherein the one or more artifacts comprise a metal artifact.

* * * * *